United States Patent [19]
Benedict et al.

[11] Patent Number: 5,953,130
[45] Date of Patent: Sep. 14, 1999

[54] MACHINE VISION METHODS AND APPARATUS FOR MACHINE VISION ILLUMINATION OF AN OBJECT

[75] Inventors: George Benedict, Alameda; Michael Jones, Dublin, both of Calif.

[73] Assignee: Cognex Corporation, Natick, Mass.

[21] Appl. No.: 08/779,312

[22] Filed: Jan. 6, 1997

[51] Int. Cl.[6] ................................................. G01N 21/84
[52] U.S. Cl. ............................................ 356/429; 356/430
[58] Field of Search .................................. 356/429, 430, 356/431, 239.1, 240, 237.1; 348/131, 370

[56] References Cited

U.S. PATENT DOCUMENTS

| | | |
|---|---|---|
| 3,816,722 | 6/1974 | Sakoe et al. . |
| 3,936,800 | 2/1976 | Ejiri et al. . |
| 3,967,100 | 6/1976 | Shimomura . |
| 3,968,475 | 7/1976 | McMahon . |
| 3,978,326 | 8/1976 | Shimomura . |

(List continued on next page.)

FOREIGN PATENT DOCUMENTS

| | | |
|---|---|---|
| 0 527 632 A2 | 2/1993 | European Pat. Off. . |
| WO 95/122137 | 8/1995 | WIPO . |
| WO 95/21376 | 8/1995 | WIPO . |
| WO 97/21189 | 6/1997 | WIPO . |
| WO 97/22858 | 6/1997 | WIPO . |
| WO 97/24692 | 7/1997 | WIPO . |
| WO 97/24693 | 7/1997 | WIPO . |

OTHER PUBLICATIONS

Grimson, W. Eric L. and Huttenlocher, Daniel P., "On the Sensitivity of the Hough Transform for Object Recognition", May 1990, IEEE Transactions on Pattern Analysis and Machine Intelligence, vol. 12, No. 3.

Medina–Mora et al.(1981) An Incremental Programming Environment, IEEE Transactions on Software Eng. SE–7:472–482.

Picture Tel Corporation Product Brochure "Picturel Live PCS 100 (tm) Personal Visual Communications System," 3 pp. (1993).

Picture Tel Corporation Product Brochure "Picturetel System 1000: Complete Videoconferencing for Cost Sensitive Applications," 4 pp. (1993).

Picture Tel Corporation Product Brochure, "Picturetel System 4000(tm) A Family of Models to Fit Your Application From Offices to Boardrooms, Classrooms, and Auditoriums," 4 pp. (1993).

Symantec Corporation, "The Norton pcAnywhere User's Guide," Table of Contents 8 pp; Introduction of pcAnywhere Technology pp. i–vii; Chapter 7–Sessions; pp. 191–240 (1991).

Bursky, Dave, "CMOS Four–Chip Set Process Images at 20–MHz Data Rates," Electronic Design, May 28, 1987, pp. 39–44.

Plessey Semiconductors, Preliminary Information, May 1986, Publication No. PS2067, May 1986, pp. 1–5.

Horn, Berthold Klaus Paul. "Robot Vision", The Massachusetts Institute for Technology, 1986.

Rosenfeld, Azriel. "Computer Vision: Basic Principles,"Proceedings of the IEEE. vol. 76, No. 8, Aug. 1988. pp. 863–868.

*Primary Examiner*—Frank G. Font
*Assistant Examiner*—Michael P. Stafira
*Attorney, Agent, or Firm*—David J. Powsner

[57] ABSTRACT

The invention provides methods and apparatus for machine vision illumination by moving a non-diffuse light beam over selected points on the object so that each is illuminated at substantially the same angle by multiple rays during acquisition of an image frame. An apparatus for illuminating an object to facilitate its being imaged by an image acquisition device, e.g., a camera, includes a radiation source that generates and transmits to a region of the a non-diffuse beam of imaging radiation having a non-point cross-section. A dithering element moves the beam so that at least a region of the object is illuminated at substantially the same angle by multiple rays during an image acquisition period.

30 Claims, 7 Drawing Sheets

U.S. PATENT DOCUMENTS

| | | | |
|---|---|---|---|
| 4,011,403 | 3/1977 | Epstein et al. | 348/370 |
| 4,115,702 | 9/1978 | Nopper . | |
| 4,115,762 | 9/1978 | Akiyama et al. . | |
| 4,183,013 | 1/1980 | Agrawala et al. . | |
| 4,200,861 | 4/1980 | Hubach et al. . | |
| 4,254,400 | 3/1981 | Yoda et al. . | |
| 4,300,164 | 11/1981 | Sacks . | |
| 4,385,322 | 5/1983 | Hubach et al. . | |
| 4,441,124 | 4/1984 | Heebner et al. . | |
| 4,441,206 | 4/1984 | Kuniyoshi et al. . | |
| 4,534,813 | 8/1985 | Williamson et al. . | |
| 4,541,116 | 9/1985 | Lougheed . | |
| 4,570,180 | 2/1986 | Baier et al. . | |
| 4,577,344 | 3/1986 | Warren et al. . | |
| 4,581,762 | 4/1986 | Lapidus et al. . | |
| 4,606,065 | 8/1986 | Beg et al. . | |
| 4,617,619 | 10/1986 | Gehly . | |
| 4,630,306 | 12/1986 | West et al. . | |
| 4,688,088 | 8/1987 | Hamazaki et al. . | |
| 4,706,168 | 11/1987 | Weisner . | |
| 4,728,195 | 3/1988 | Silver . | |
| 4,730,260 | 3/1988 | Mori et al. . | |
| 4,731,858 | 3/1988 | Grasmueller et al. . | |
| 4,736,437 | 4/1988 | Sacks et al. . | |
| 4,742,551 | 5/1988 | Deering . | |
| 4,764,870 | 8/1988 | Haskin . | |
| 4,771,469 | 9/1988 | Wittenburg . | |
| 4,783,826 | 11/1988 | Koso . | |
| 4,783,828 | 11/1988 | Sadjadi . | |
| 4,783,829 | 11/1988 | Miyakawa et al. . | |
| 4,831,580 | 5/1989 | Yamada . | |
| 4,860,374 | 8/1989 | Murakami et al. . | |
| 4,860,375 | 8/1989 | McCubbrey et al. . | |
| 4,876,457 | 10/1989 | Bose . | |
| 4,876,728 | 10/1989 | Roth . | |
| 4,903,218 | 2/1990 | Longo et al. . | |
| 4,907,169 | 3/1990 | Lovoi . | |
| 4,914,553 | 4/1990 | Hamada et al. . | |
| 4,922,543 | 5/1990 | Ahlbom et al. . | |
| 4,926,492 | 5/1990 | Tanaka et al. . | |
| 4,932,065 | 6/1990 | Feldgajer . | |
| 4,953,224 | 8/1990 | Ichinose et al. . | |
| 4,955,062 | 9/1990 | Terui . | |
| 4,959,898 | 10/1990 | Landman et al. . | |
| 4,962,423 | 10/1990 | Yamada et al. . | |
| 4,972,359 | 11/1990 | Silver et al. . | |
| 4,982,438 | 1/1991 | Usami et al. . | |
| 5,012,402 | 4/1991 | Akiyama . | |
| 5,046,190 | 9/1991 | Daniel et al. . | |
| 5,054,096 | 10/1991 | Beizer . | |
| 5,060,276 | 10/1991 | Morris et al. . | |
| 5,063,608 | 11/1991 | Siegel . | |
| 5,073,958 | 12/1991 | Imme . | |
| 5,081,656 | 1/1992 | Baker et al. . | |
| 5,081,689 | 1/1992 | Meyer et al. . | |
| 5,086,478 | 2/1992 | Kelly-Mahaffey et al. . | |
| 5,090,576 | 2/1992 | Menten . | |
| 5,091,861 | 2/1992 | Geller et al. . | |
| 5,091,968 | 2/1992 | Higgins et al. . | |
| 5,093,867 | 3/1992 | Hori et al. . | |
| 5,113,565 | 5/1992 | Cipolla et al. . | |
| 5,115,309 | 5/1992 | Hang . | |
| 5,119,435 | 6/1992 | Berkin . | |
| 5,124,622 | 6/1992 | Kawamura et al. . | |
| 5,133,022 | 7/1992 | Weideman . | |
| 5,134,575 | 7/1992 | Takagi . | |
| 5,143,436 | 9/1992 | Baylor et al. . | |
| 5,145,432 | 9/1992 | Midland et al. . | |
| 5,151,951 | 9/1992 | Ueda et al. . | |
| 5,153,925 | 10/1992 | Tanioka et al. . | |
| 5,159,281 | 10/1992 | Hedstrom et al. . | |
| 5,159,645 | 10/1992 | Kumagai . | |
| 5,164,994 | 11/1992 | Bushroe . | |
| 5,168,269 | 12/1992 | Harlan . | |
| 5,172,005 | 12/1992 | Cochran et al. | 356/430 X |
| 5,185,855 | 2/1993 | Kato et al. . | |
| 5,189,712 | 2/1993 | Kajiwara et al. . | |
| 5,206,820 | 4/1993 | Ammann et al. . | |
| 5,216,503 | 6/1993 | Paik . | |
| 5,225,940 | 7/1993 | Ishii et al. . | |
| 5,230,027 | 7/1993 | Kikuchi . | |
| 5,243,607 | 9/1993 | Masson et al. . | |
| 5,253,306 | 10/1993 | Nishio . | |
| 5,253,308 | 10/1993 | Johnson . | |
| 5,265,173 | 11/1993 | Griffin et al. . | |
| 5,271,068 | 12/1993 | Ueda et al . | |
| 5,287,449 | 2/1994 | Kojima . | |
| 5,297,256 | 3/1994 | Wolstenholme et al. . | |
| 5,299,269 | 3/1994 | Gaborski et al. . | |
| 5,311,598 | 5/1994 | Bose et al. . | |
| 5,315,388 | 5/1994 | Shen et al. . | |
| 5,319,457 | 6/1994 | Nakahashi et al. . | |
| 5,327,156 | 7/1994 | Masukane et al. . | |
| 5,337,267 | 8/1994 | Colavin . | |
| 5,363,507 | 11/1994 | Nakayama et al. . | |
| 5,367,439 | 11/1994 | Mayer et al. . | |
| 5,367,667 | 11/1994 | Wahlquist et al. . | |
| 5,371,690 | 12/1994 | Engel et al. . | |
| 5,388,197 | 2/1995 | Rayner . | |
| 5,388,252 | 2/1995 | Dreste et al. . | |
| 5,398,292 | 3/1995 | Aoyama . | |
| 5,432,525 | 7/1995 | Maruo et al. . | |
| 5,440,699 | 8/1995 | Farrand et al. . | |
| 5,455,870 | 10/1995 | Sepai et al. . | |
| 5,455,933 | 10/1995 | Schieve et al. . | |
| 5,475,766 | 12/1995 | Tsuchiya et al. . | |
| 5,477,138 | 12/1995 | Efjavic et al. . | |
| 5,481,712 | 1/1996 | Silver et al. . | |
| 5,485,570 | 1/1996 | Bushboom et al. . | |
| 5,491,780 | 2/1996 | Fyles et al. . | |
| 5,495,424 | 2/1996 | Tokura . | |
| 5,495,537 | 2/1996 | Bedrosian et al. . | |
| 5,519,840 | 5/1996 | Matias et al. . | |
| 5,526,050 | 6/1996 | King et al. . | |
| 5,532,739 | 7/1996 | Garakani et al. . | |
| 5,550,763 | 8/1996 | Michael . | |
| 5,566,877 | 10/1996 | McCormack . | |
| 5,568,563 | 10/1996 | Tanaka et al. . | |
| 5,574,668 | 11/1996 | Beaty . | |
| 5,574,801 | 11/1996 | Collet-Beillon . | |
| 5,583,949 | 12/1996 | Smith et al. . | |
| 5,583,954 | 12/1996 | Garakani . | |
| 5,592,562 | 1/1997 | Rooks . | |
| 5,594,859 | 1/1997 | Palmer et al. . | |
| 5,602,937 | 2/1997 | Bedrosian et al. . | |
| 5,608,872 | 3/1997 | Schwartz et al. . | |
| 5,640,199 | 6/1997 | Garakani et al. . | |
| 5,640,200 | 6/1997 | Michael . | |

MACHINE VISION METHODS AND APPARATUS FOR MACHINE VISION ILLUMINATION OF AN OBJECT

BACKGROUND OF THE INVENTION

The invention pertains to machine vision and, more particularly, to methods and apparatus for illuminating objects under inspection. The invention has application in machine vision inspection of stationary and moving objects, such as moving webs.

Machine vision refers to the automated analysis of images to determine characteristics of objects shown in them. One of its applications is in web manufacture, where continuous sheets are inspected for defects as they move from station to station or as they are rolled for shipping. For example, in the manufacture of sheet metal, images are analyzed to insure that the sheets are not scratched or otherwise defective.

Machine vision has wide application in other industries as well. It can be used in the semiconductor device industry, for example, to analyze images of boards, chips and other components to verify their integrity. It can also be used in the paper industry to detect blemishes on or near the surface of the paper.

The prior art suggests the use of "dark field" imaging to facilitate the detection on the surfaces of objects of features (or defects) that cast shadows such a scratches, rips, dents or lumps. According to this technique, an imaging device (e.g., camera) is placed outside the usual pathway along which light from the illuminating source is reflected from the object.

Dark field imaging is effective because it highlights features or defects that protrude from (or into) the surface of the object being inspected. A dark field image of a smooth reflective semiconductor surface, for example, is uniformly dark, since none of the light from the illumination source is reflected to the camera. If that surface is scratched, however, light reflecting from the edges of the scratch is reflected to the camera, thereby, revealing the imperfection.

To date, the art has had only limited success in applying dark field imaging to the inspection of moving webs. One prior art scheme calls for aiming a camera along a line normal to the surface of a web that is illuminated obliquely with diffuse light, e.g., a fluorescent tube. A problem with this arrangement is that the images typically fail to reveal all but the grossest defects in the material.

Another prior art scheme for illuminating moving webs is laser sidelighting. According to that technique, a beam of non-diffuse light, e.g., laser light, is used to illuminate the web obliquely from the side, while a camera images the web along a line normal to the surface of the web. A problem with laser sidelighting is that it brings out so much detail in the web itself that extraordinary processing power and time is required to identify the defects. Another problem is that interference between the reflected rays of laser light causes artifacts (e.g., a speckle pattern consisting of "sparkles" or dots) that further complicate analysis.

In view of the foregoing an object of this invention is to provide improved methods and apparatus for machine vision and, particularly, improved methods and apparatus for illuminating objects under inspection.

A further object of the invention is to provide such improved methods and apparatus as can be applied in dark field imaging of objects, such as moving webs, to highlight characteristics of interest, e.g., defects.

Yet another object of the invention is to provide such methods and apparatus as are suitable for highlighting characteristics of interest without unduly highlighting those that are not of interest.

Still another object of the invention is to provide such methods and apparatus as can be used with "line" cameras, i.e., cameras that generate images of linear (vs planar) fields of view, as well as conventional planar field of view cameras.

Yet still another object of the invention is to provide such methods and apparatus as can be implemented without undue cost and use of specialized equipment.

SUMMARY OF THE INVENTION

The aforementioned objects are among those attained by the invention which provides methods and apparatus for machine vision illumination by moving a non-diffuse light beam over selected regions of an object so that each is illuminated at the same (or substantially the same) angle by multiple rays during acquisition of an image frame.

In one aspect, the invention provides a system for illuminating an object to facilitate its being imaged by an image acquisition device, e.g., a camera. The system includes a radiation source (e.g., a laser) that generates and transmits to a region on the object a non-diffuse beam of imaging radiation having a non-point cross-section. A dithering element moves the beam (e.g., via moving the illumination source itself, or via use of lenses and/or mirrors) so that points in the region are illuminated at the same (or substantially the same) angle by multiple rays from the beam during the "image frame acquisition period," i.e., the period of time during which the image acquisition device (e.g., video camera) generates a single frame image of the object.

According to one aspect of the invention, the radiation source is a laser whose point-source output is passed through one or more lenses (e.g., spherical and/or cylindrical lenses) to produce a linear, circular or other beam of non-point cross-section beam which is directed at the region of the object to be imaged. The dithering element can include, for example, an oscillatory lens (or mirror) and a collimating lens (or mirror), through which the beam passes on its way to the object.

As used herein, the image frame acquisition period is the period of time during which the image acquisition generates a single frame of an image of the object. For example, if the image acquisition device is a conventional single lens reflex (SLR) camera, the image acquisition period it the length of time that the shutter opens to gather a single image of the object (e.g., one-thirtieth of a second for a shutter speed of "30," one-quarter of a second for a shutter speed of "4," and so forth). For a preferred image acquisition device, i.e., a video "line" camera, the image acquisition period is typically 0.00010 seconds.

Further aspects of the invention provide an illumination system as described above in which the beam illuminates the object so as to provide dark field illumination with respect to the image acquisition device. Thus, for example, the dithering element can transmit the non-diffuse beam at a grazing (or oblique) angle with respect to the surface of the object, e.g., if the image acquisition device is aimed along a line normal to the surface of the object.

In still further aspects, the invention provides an illumination system as described above in which the radiation source generates and transmits multiple distinct non-diffuse, non-point cross-section beams of imaging radiation to the object. In this regard, for example, the radiation source can employ two laser sources providing non-diffuse beams at differing angles.

An illumination system as described above can also include a source of diffuse radiation, e.g., a fluorescent light, for illuminating the object being imaged. That source, too, can provide dark field illumination with respect to the image acquisition device. Thus, for example, the diffuse radiation source can transmit diffuse radiation at a grazing (or oblique) angle with respect to the surface of the object, e.g., if the image acquisition device is aimed along a line normal to the surface of the object.

Still further aspects of the invention provide methods of illumination paralleling the operations of the systems described above.

The invention has wide application in industry and research applications. It facilitates the illumination of objects under inspection so that resulting images can be readily inspected for the presence of characteristics, such as defects. Thus, for example, an illumination system in accord with the invention can be used to provide dark-field illumination for inspection of moving webs (e.g., in sheet metal manufacture) so that they can be automatically examined for flaws.

These and other aspects of the invention are evident in the drawings and in the description that follows.

BRIEF DESCRIPTION OF THE DRAWINGS

A more complete understanding of the invention may be attained by reference to the drawings, in which.

DETAILED DESCRIPTION OF THE ILLUSTRATED EMBODIMENT

Figure 1:
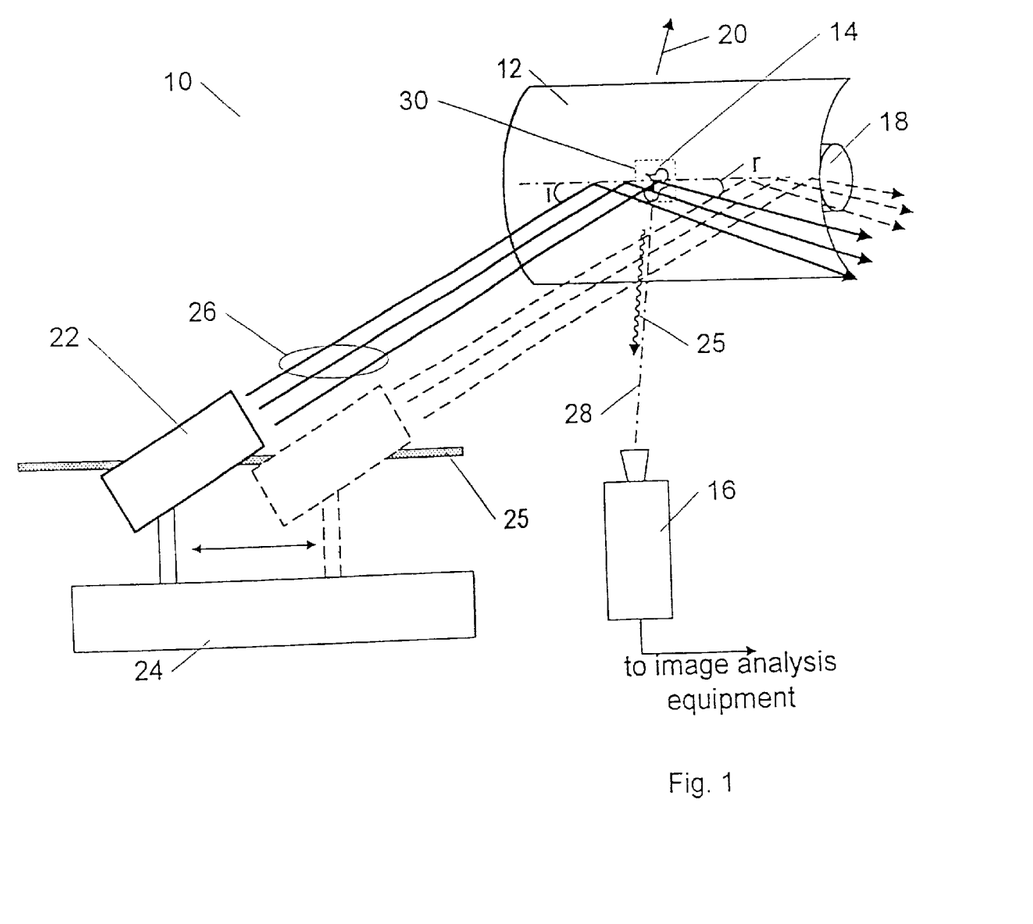
FIG. 1 depicts an embodiment of the invention employing a single, non-diffuse radiation source and a dithering element for moving the source and its beam.

FIG. 1 depicts an illumination system 10 according to one practice of the invention for illuminating an object 12 to facilitate identification of a characteristic 14 thereon in images generated by image acquisition device 16 and processed by image analysis equipment (not shown). In the illustration, object 12 is shown as a web, e.g., a sheet metal roll, under manufacture and moving across a roller 18 in the direction as indicated by arrow 20. The illustrated characteristic 14 is a scratch or undesirable blemish in the web.

Notwithstanding the details of the illustration, those skilled in the art will appreciate that the invention has application in inspection of objects other then webs (e.g., semiconductor surfaces, printed circuit boards, papers, and other articles of manufacture), regardless of whether they are moving at the time of inspection.

The illumination system 10 includes a non-diffuse illumination source 22 and a dithering element 24. The non-diffuse source 22 is a laser or any other source of non-diffuse radiation, e.g., a frequency-shifted laser. Dithering element 24 moves the illumination source 22 along track 25 and, therefore, the beam 26 so that at least selected points (or region) on the surface of object 12 are illuminated at the same (or substantially the same) angle by multiple rays from the beam during acquisition of a single image frame.

The source 22 is aimed to provide dark field illumination to the object 12 with respect to image acquisition device 16. Thus, the beam 26 is directed such that the angle of incidence i and natural angle of reflection r are not on the line of aim 28 of image acquisition device 16. Those skilled in the art will, of course, appreciate that any other relationship of source 22, object 12 and acquisition device 16 that results in dark field illumination may also be employed. Because the source 22 is arranged to provide dark field illumination, only radiation from beam 26 that falls upon and is reflected from perturbations on the surface of object 12 reach image acquisition device 16. Thus, for example, radiation falling on feature 14 is reflected to device 16, as indicated by ray 25.

Figure 5:
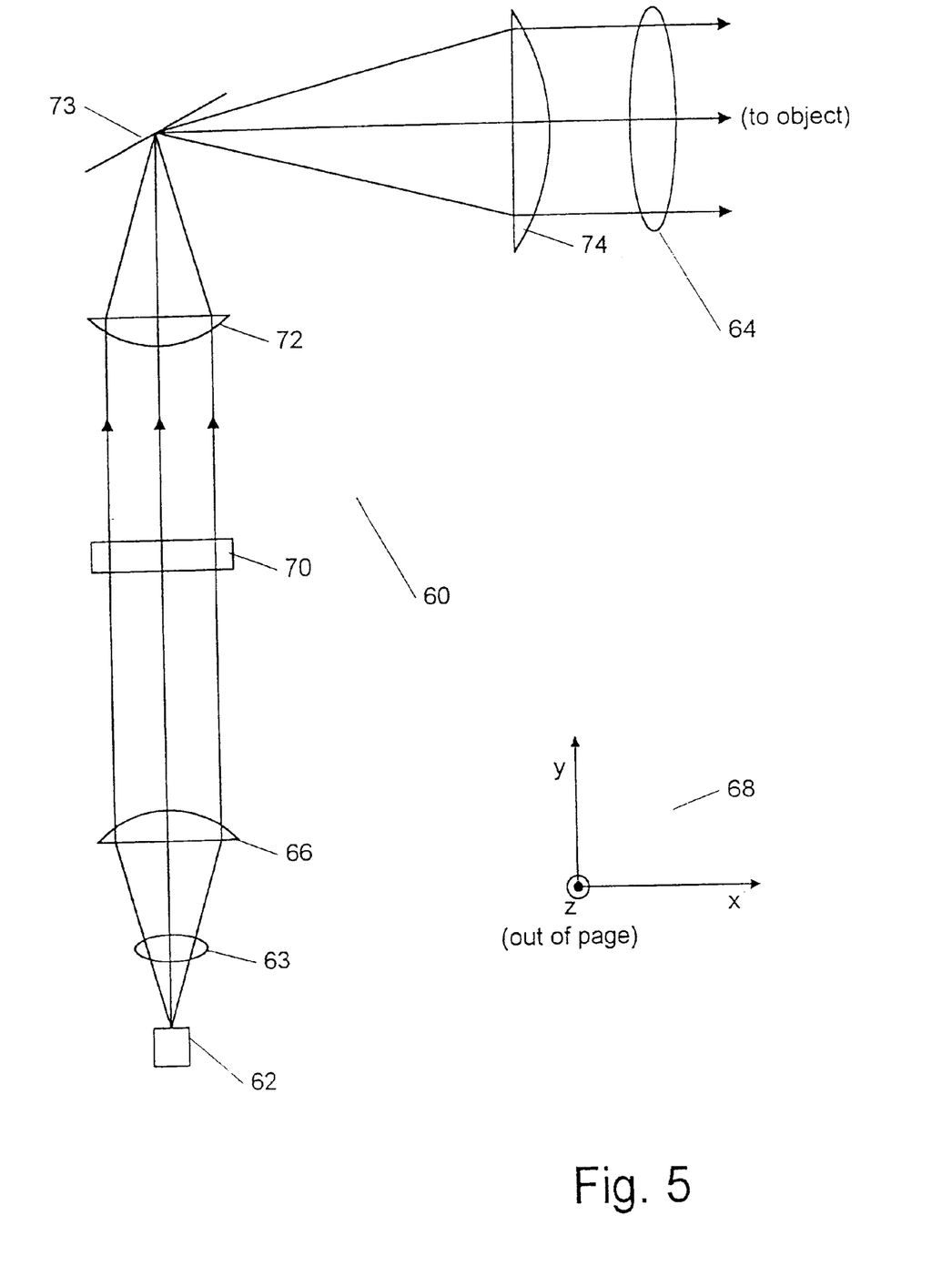
FIG. 5 depicts a preferred optical arrangement for dithering a beam of non-diffuse light in an apparatus according to the invention.

The beam 26 has a non-point cross-section, e.g., a linear, rectilinear, circular, oval, or other one or two-dimensional form. As shown in FIG. 5 and discussed below, for example, a linear (or rectilinear) cross-section can be generated by applying the pointsource output of a conventional laser to one or more spherical and/or cylindrical lens. The dimensions of the cross-section, particularly, in the direction of motion of the beam are selected in accord with the oscillatory rate of the dithering element and the frame acquisition rate of the image acquisition device 26.

With reference to FIG. 1, the dithering element 24 moves the beam 26 across the object 12 and, particularly, across region or regions thereof to be inspected. Those regions may be on the surface of the object 12, as depicted in the drawing, or underneath that surface (e.g., with an appropriately selected illumination source 22). For sake of convenience, in the discussion that follows the region to be inspected is labelled 30. Those skilled in the art will appreciate that the teachings herein can be applied to inspection of a larger region, e.g., one encompassing the entire width of object 12.

The illustrated dithering element 24 is an oscillating motorized arm that moves the illumination source 22 back-and-forth along track 25 and, thereby, moves beam 26 so that multiple rays of the beam strike region 30 from the same (or substantially the same) angle during an image frame acquisition period. This movement of the beam is more particularly illustrated in FIGS. 2A–2E.

Those skilled in the art will appreciate that the dithering element can be implemented as any mechanical, electromechanical, optical, electro-optical, mechano-optical element that causes the beam to move over the region 30 in this manner. In a preferred embodiment shown in FIG. 5, for example, the dithering element is an oscillating mirror that reflects the non-diffuse beam through a collimating lens. It will also be appreciated that the dithering element 24 can be part of the illumination source 22 itself or it can be a separate element, as illustrated herein for sake of convenience.

FIGS. 2A–2E illustrate movement of the beam 26 over region 30 during generation of a single image frame of object 12 by image acquisition device 16. Particularly, the drawings illustrate that the dithering element 24 moves the beam 26 over region 30 such that each point therein is illuminated by multiple rays of the beam from substantially the same angle during acquisition of a single image frame.

Figure 2A:
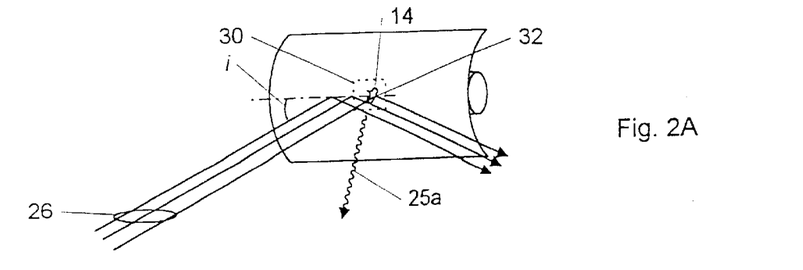
FIGS. 2A–2E depict the motion of a non-diffuse beam over an object under inspection in an apparatus according to the invention.

Thus, as shown in FIG. 2A, a point 32 on the surface of object 12 (and, particularly, on feature 14) is illuminated by beam 26 at an angle i. This occurs, e.g., at the start of a time period during which the image acquisition device generates a single frame image of the object 12. Radiation incident on point 32—which for present purposes is treated as a perturbation—is reflected to the image acquisition device, as indicated by ray 25a.

Figure 2B:
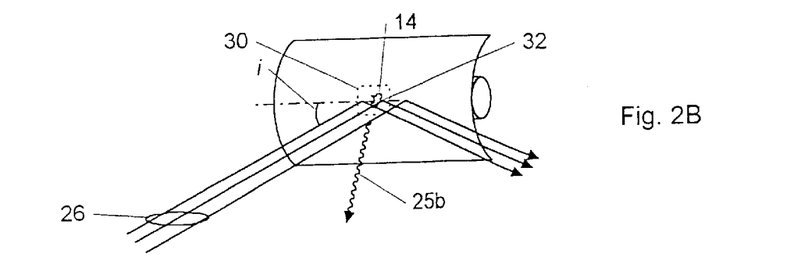

As shown in FIG. 2B, subsequently during that period, dithering element 24 moves the beam (e.g., along with the radiation source) so that the point 32 is illuminated at substantially the same angle i, albeit by a different portion or ray of the beam 26. Radiation incident on point 32 is reflected to the image acquisition device as ray 25b.

Figure 2C:
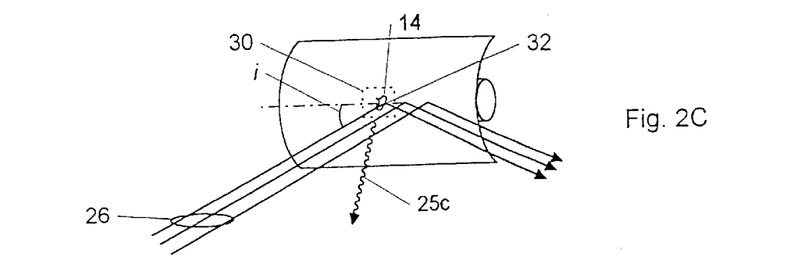

As shown in FIG. 2C, the dithering element 24 moves the beam 26 still further during that period so that the point 32 is illuminated by yet another ray in beam 26 at angle i. Radiation incident on point 32 is reflected to the image acquisition device as ray 25c.

Figure 2D:
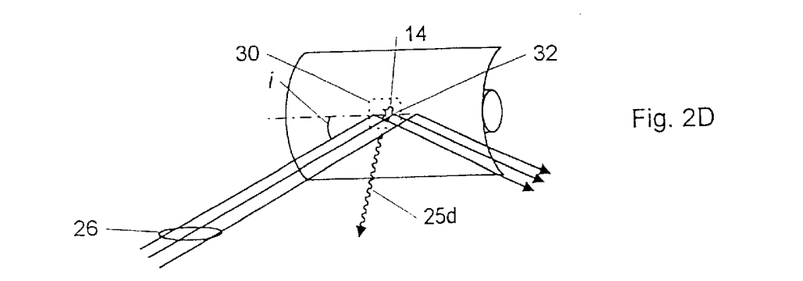

As shown in FIG. 2D, the dithering element 24 then begins to move the beam 26 back during the image frame acquisition period so that the point 32 is illuminated by yet another portion or ray, again, at angle i. Radiation incident on point 32 is reflected to the image acquisition device as ray 25d.

Figure 2E:
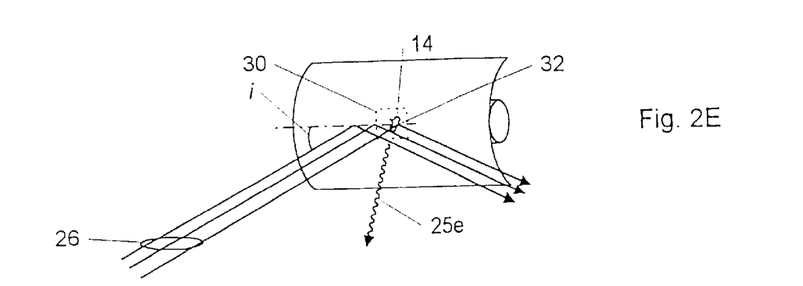

Moreover, as shown in FIG. 2E, the dithering element 24 continues to move the beam 26 during the period so that the point 32 is again illuminated at angle i by another ray. Radiation incident on point 32 is reflected to the image acquisition device as ray 25e.

In this manner, the dithering element moves the beam 26 over the region 30 so that it is illuminated at substantially the same angle by multiple rays or portions of the beam during generation of a single image frame. Other modes of motion or beam generation may also be used to provide such illumination. For example, the beam can be moved randomly or in any other periodic or non-periodic mode over the region to be illuminated. Moreover, though preferred, the beam need not be constantly "on" during the entire period when each image frame is generated. Rather, the beam can be turned on and off sporadically or periodically so long as during generation of at least one image frame selected points on object 12 are illuminated by multiple portions or rays from beam 26 at substantially the same angle.

Figure 3:
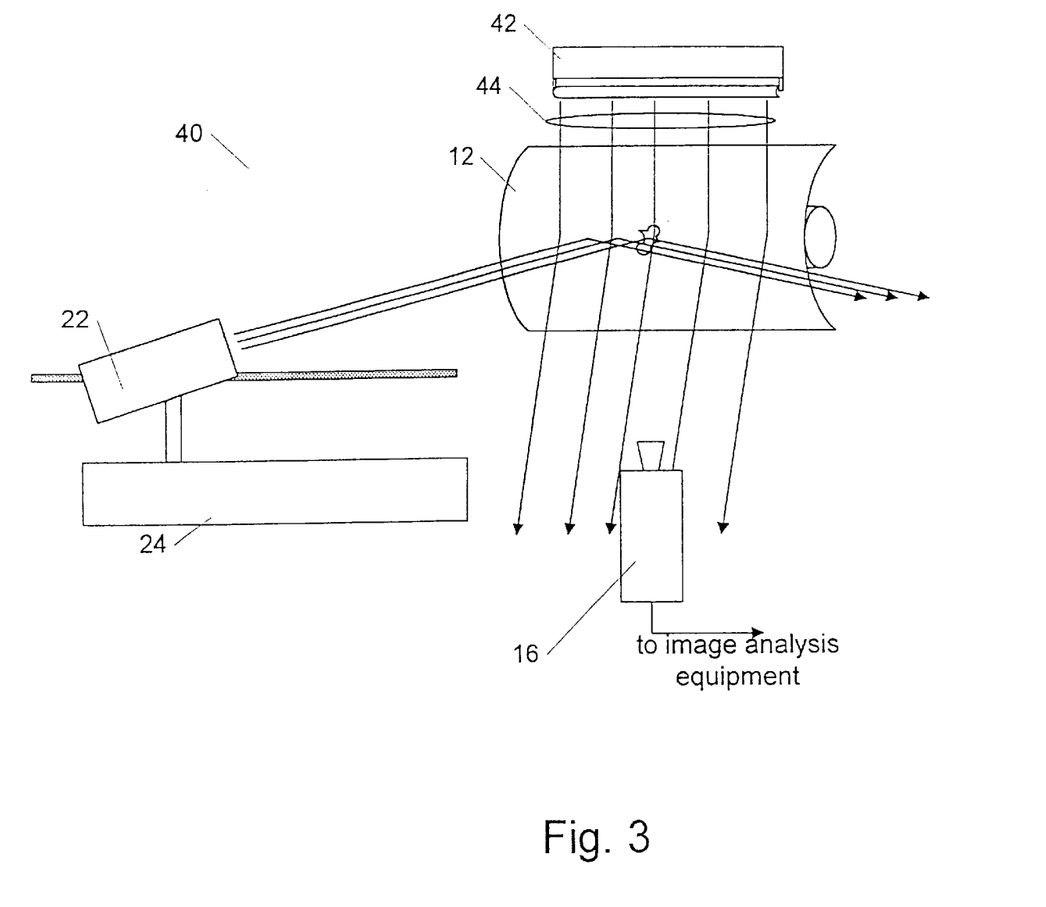
FIGS. 3 and 4 depict alternate embodiments of the invention employing multiple radiation sources.

FIG. 3 depicts an illumination system 40 according to another practice of the invention for illuminating an object 12 to facilitate identification of a characteristic 14 thereon in images generated by image acquisition device 16 and processed by image analysis equipment (not shown). The system is constructed and operated identically to that shown in FIG. 1 (as indicated by the use of like elemental designations) except insofar as it includes additional illumination source 42.

Illumination source 42 generates diffuse radiation that, too, is arranged to provide dark field illumination to the object 12 with respect to image acquisition device 16. Thus, the beams 44 generated by source 42 are directed such that their angle of incidence and natural angle of reflection are not on the line of aim of image acquisition device 16. For example, as shown in the illustration, image acquisition device 16 is aimed along a line normal to the surface of object 12, while source 42 generates beams 44 that strike the surface of object 12 at oblique angles. Those skilled in the art will, of course, appreciate that any other relationship of source 42 that provides for dark field illumination with respect to image acquisition device 16 can also be used. The illumination source 42 may be a fluorescent tube, a fiber optic light line, or any other source of diffuse radiation.

Figure 4:
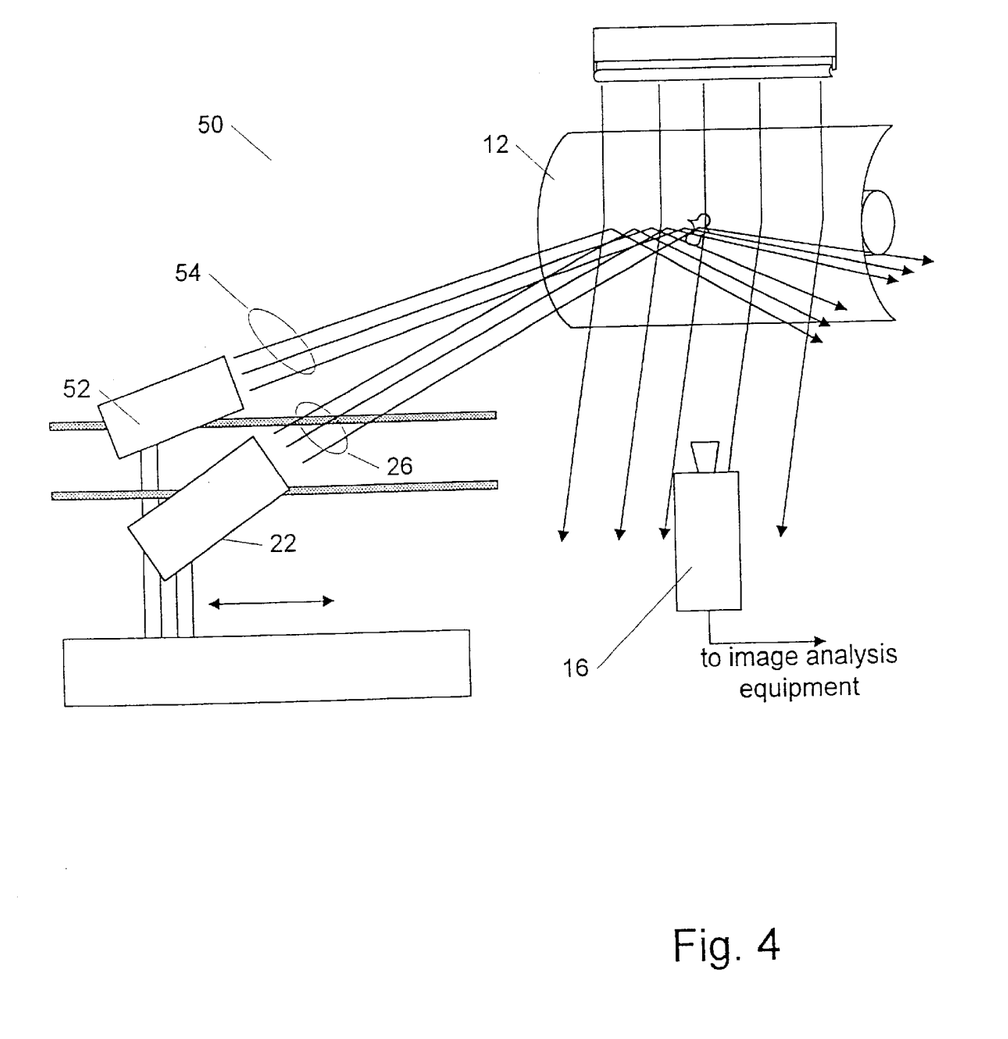

FIG. 4 depicts an illumination system 50 according to another practice of the invention for illuminating an object 12 to facilitate identification of a characteristic 14 thereon in images generated by image acquisition device 16 and processed by image analysis equipment (not shown). The system is constructed and operated identically to that shown in FIG. 3 (as indicated by the use of like elemental designations) except insofar as it includes two non-diffuse illumination sources 22 and 52.

The second non-diffuse source 52 is constructed and operated identically to source 22, i.e., to generate non-diffuse radiation for dark field illumination to the object 12 with respect to image acquisition device 16. Source 52, however, supplies a beam 54 of non-diffuse radiation that impinges on object 12 at an angle different than that of beam 26 of source 22. Though beam 54 (and its source 52) is shown as being moved across object 12 via the same dithering element 24, it will be appreciated that beam 54 may be moved via a separate and distinct dithering element.

Figure 6A:
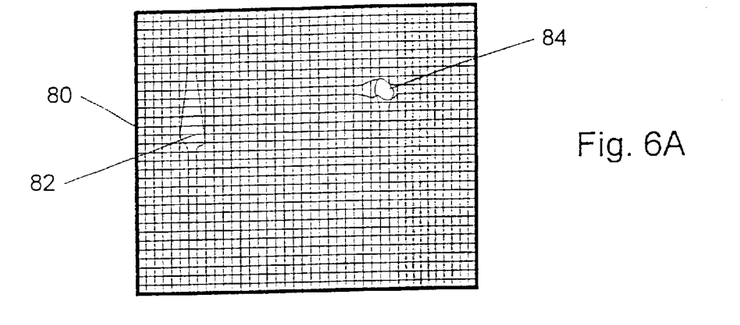
FIGS. 6A–6D illustrate the comparative effects of invention in illuminating a web for defects.
Figure 6B:
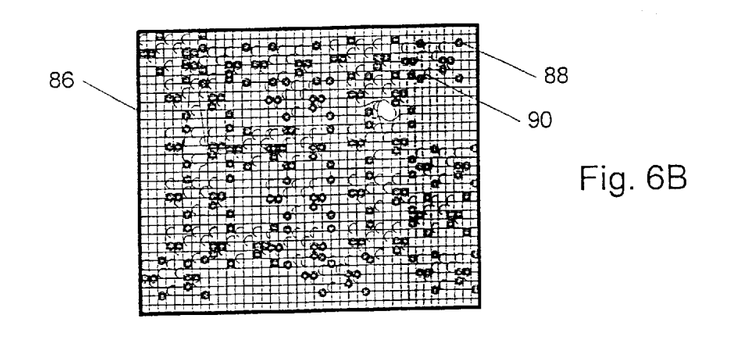

A further appreciation of the invention may be had by reference to FIGS. 6A–6D, where there are shown the beneficial effects of the invention are illustrated. At the outset, referring to FIG. 6A, there is depicted a portion 80 of a web, e.g., sheet metal roll, of the type that can be illuminated by methods and apparatus according to the invention. The figure depicts not only defects 82 and 84, but also a cross-hatched pattern representing a background characteristic that may be present on the surface of the web. Those skilled in the art will appreciate that many web defects, such as 82, 84, are normally not visible to the naked eye or to a conventional camera under prior art lighting conditions. FIG. 6B depicts an image 86 of web 80 as produced using a prior art laser-sidelight dark field imaging. As shown in the drawing, many of the details in the web 80 are obscured by interference patterns and speckle patterns, illustrated as dots 88 and lines (not shown), that result from incidence of conventional coherent lighting on the web. Therefore, analysis of image 86 for the existence and properties of features 82, 84 will be exceedingly processor intensive and time consuming.

Figure 6C:
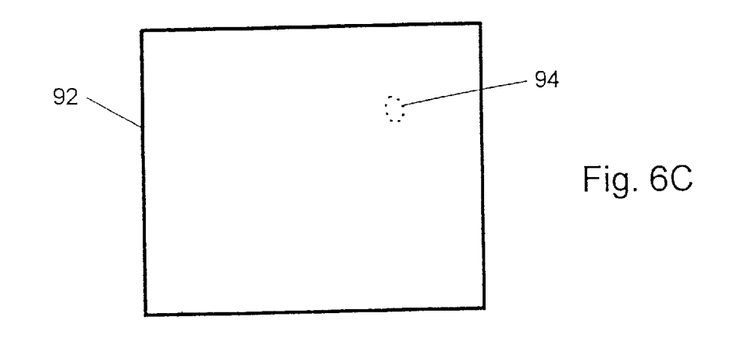

FIG. 6C depicts an image 92 of web 80 as produced using a prior art diffuse-light dark imaging. As shown in the drawing, not only are the details of the web 80 lost, but so is the information regarding the features 82, 84. Particularly, under diffuse sidelighting, only the rough outline 94 of one of the features is visible. Accordingly, analysis of image 92 for the existence and properties of features 82, 84 will not provide complete information.

Figure 6D:
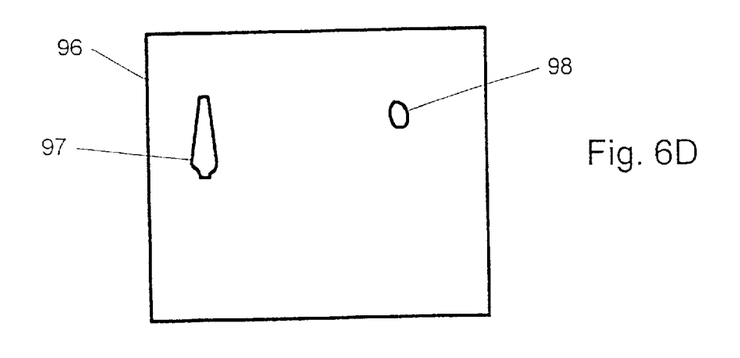

FIG. 6D depicts an image 96 of the web 80 as produced utilizing illumination apparatus and methods according to the invention. Particularly, through use of any of the arrangements shown in FIGS. 1, 3 and 4, hereof, features 82, 84 are highlighted—as shown by outlines 97, 98—while details of the web background itself are not. As a result, analysis of image 96 to identify the existence and characteristics of features 82, 84 can be accomplished quickly, completely and without undue consumption of resources.

FIG. 5 depicts a preferred arrangement 60 according to the invention for generating a non-point cross-section beam of non-diffuse radiation and moving that beam rapidly across the object to be inspected so that a region to be inspected is illuminated at the same angle by multiple rays in the beam. The arrangement 60 may be substituted, e.g., for elements 22, 24, and 25 of FIG. 1, in order to generate the beam 26.

Arrangement 60 includes a source 62 of non-diffuse radiation, typically, one that generates a beam with a point cross-section. This can be a conventional, commercially available laser or other non-diffuse radiation source. A beam 63 generated by that source is collimated by a conventional collimating lens 66, as shown.

The resulting collimated beam passes through a cylindrical lens 72 that focuses the beam at the mirror 24 along one axis. Taking FIG. 5 as a top view, the cylinder lens 70 focuses the beam at the mirror 24 along the vertical axis (or the z-axis), as indicated by coordinate frame 68. The spherical lens 74 collimates both the cylinder lenses 70, 72 so that the beam has a desired height (z-axis) and width (x-axis) when it ultimately impinges on object 12. As above, those skilled in the art will appreciate that mirrors or other optical, mechano-optical, electro-optical or other elements capable of focussing the beam may be used in place of lenses 66, 70, 72, 74.

Once focussed, the beam impinges on and is reflected from an oscillating mirror 73 which, together with collimating lens 74, serves in place of the dithering element 24. Particularly, mirror 73 rotates, jitters, or otherwise moves so as the change the angle with which the beam passes to the collimating lens 74. That lens, which can be for example a spherical lens, collimates the "dithered" beam so that it is effectively "folded back" over itself. As a result, different rays in the beam pass over each point in region 30 (i.e., the region of the object to be illuminated), albeit at the same angle. Thus, the combination of elements 73 and 74 have the same effect as the dithering element 24 of FIG. 1. As above, those skilled in the art will appreciate that illustrated mirror 73 may be replaced by other optical, opto-mechanical, electromechanical and other devices, e.g., an oscillating lens, that cause the beam 64 to pass to lens 74 at differing angles. Likewise, it will be appreciated that mirrors or other optical, mechano-optical, electro-optical or other elements capable of focussing the beam may be used in place of lens 74.

In an embodiment of the invention for illumination of sheet metal webs for imaging by a line camera with an effective shutter speed of 10,000 lines per second, the source 62 is a commercially available diode-type laser of the type available from Spectra Diode Labs. Collimating lens 66 is an aspheric lens having the following specifications: 0.40 N.A., 6 mm focal length, of the type commercially available from Thor Labs, placed 4.2 mm from the source 62. Cylinder lens 70 is a 250 mm focal length lens of the type commercially available from Rolyn Optics, placed 250 mm from the mirror 73. Cylinder lens 72 is a 22 mm focal length lens of the type commercially available from Rolyn Optics, placed 22 mm from the mirror 72.

Continuing with discussion of the aforementioned embodiment, dithering element 73 is a 5 mm×5 mm optical quality mirror that oscillates at a rate of 10,000 cycles per second and, preferably, at a rate of 20,000 cycles per second. The mirror is driven for such oscillations by a fixed frequency resonant electromechanical oscillator of the type commercially available from Electro-Optical Products, Corp. Other optical, opto-mechanical, electromechanical and other devices, e.g., an oscillating lens, may be used to move the beam. Collimating lens 74 is a plano-convex lens having the following specifications: 200 mm diameter, 380 mm focal length of the type commercially available from Rolyn Optics, placed 380 mm from the dithering mirror. As a result of use of such lenses, the beam 64 has a height of 8" and a width of ¼" inch. Those skilled in the art will, of course, appreciate that a multitude of other combinations of sources, lenses and spacings may be used to create a beam 64 of non-point cross section and that the specifics provided herein are merely illustrative of one such combination.

Still continuing with discussion of the aforementioned embodiment, a conventional line camera, e.g., of the type commercially available from Dalsa, Inc., is used to image the web. Of course, any other image acquisition device may be used instead, whether or not that images lines, planar fields, conventional spectrum light, or otherwise. Whereas the beam 64 is incident on the web at an angle selected between 1 and 25 degrees and, preferably, 2 and 5 degrees. A diffuse source 42, illuminates the web from above at an angle of about 20 degrees from the web normal. Again, those skilled in the art will, of course, appreciate that a multitude of other combinations of cameras, lenses and spacings may be used transmit the beam 64 to the object and to image the same.

Figure 7:
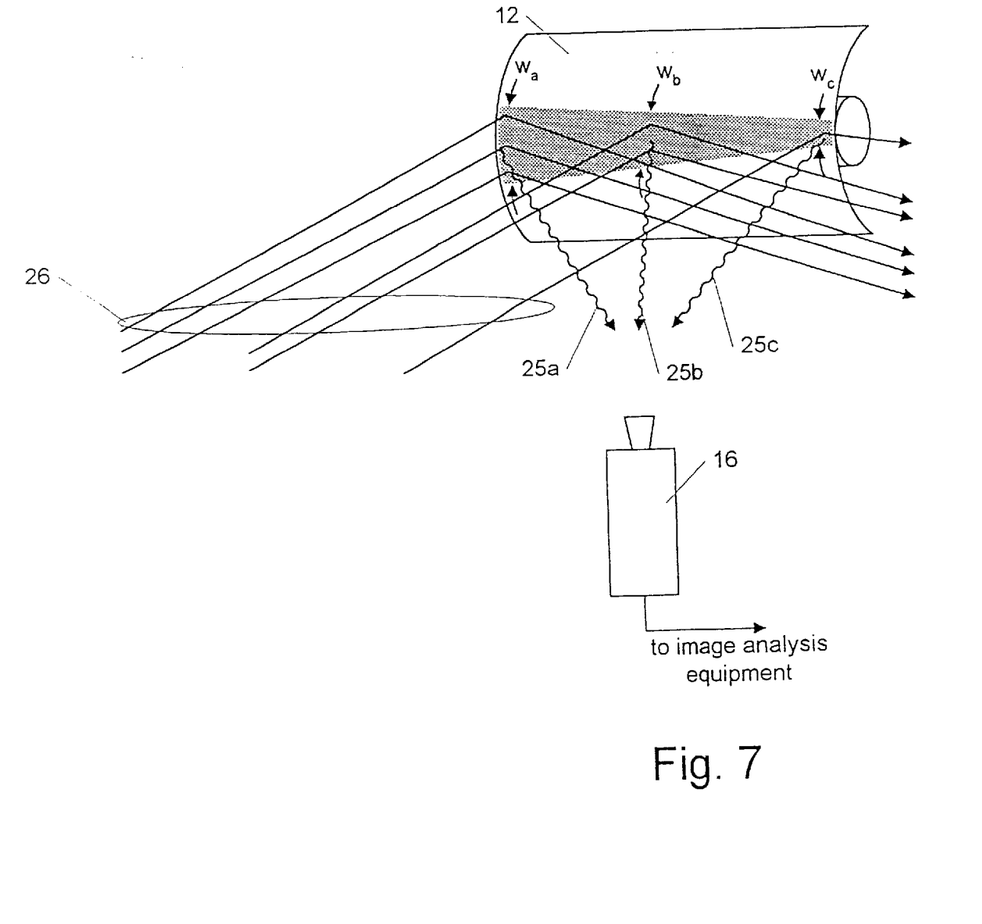
FIG. 7 depicts an embodiment of the invention employing a single, non-diffuse radiation source with a beam cross-section adapted to compensate for energy differences between back-scattered and forward-scattered radiation.

FIG. 7 depicts an illumination system according to a preferred practice of the invention where the object 12 is illuminated with a beam 26 of diminishing cross-section to compensate for differences in energy of rays 25a, 25b, 25c reflected from different angles with respect to image acquisition device 16. As those skilled in the art will appreciate, rays 25a that are scattered in the "forward" direction are stronger than those 25c that are scattered in the "backward" direction. This difference may be as much as a 3-fold to 5-fold factor for a beam 26 with rectlinear cross-section.

The illustrated embodiment compensates for reflected beam-strength differential by widening the beam cross section and, therefore, reducing its "flux," in regions from which rays 25a are forward-scattered to device 16. Conversely, the beam cross-section is narrowed and, therefore, its flux is increased, in regions from which rays 25c are "back-scattered" to device 16.

Thus, in the illustrated embodiment, beam 26 has a cross-section of width $w_a$ at a side of object 12 that is nearer the illumination source (not illustrated) and that is optically "upstream" from device 16, while it has a cross-section of width $w_c$ at a side of object 12 that is further the source of beam 26 and that is optically "downstream" from device 16, where $w_a > w_c$. The beam 26 has a cross-section of width $w_b$ at middle regions on object 12, where $w_a > w_b$ and $w_b > w_c$.

Referring to FIG. 5 and to the accompanying discussion, a beam 26 of diminishing cross-section is achieved by increasing a distance between lens 74 and mirror 73. The position of lens 72 is then adjusted to recollimate the beam in the y direction. In a preferred embodiment, $w_a$ is preferably 3 to 5 times larger then $w_c$. Those skilled in the art will, of course, appreciate that beams of other shapes may be employed to compensate for forward/backward scattering differences and/or that other ratios of beam cross-section diminishment may be used. It will also be appreciated that such differences may be compensated for by the image processing equipment itself.

Described above are improved methods and apparatus for machine vision and, particularly, improved methods and apparatus for illuminating objects under inspection meeting the objects set forth herein. These methods and apparatus permit improved dark field imaging of objects, such as moving webs, to highlight characteristics of interest, e.g., defects. These methods and apparatus are suitable for highlighting characteristics of interest without unduly highlighting those that are not of interest. They are also suitable for use with "line" cameras, as well as conventional planar-field cameras, among other image acquisition devices. Still further, these methods and apparatus can be implemented without undue cost and use of specialized equipment.

It will be appreciated that the illustrated embodiments are examples of the invention and that other embodiments incorporating modifications thereto fall within the scope of the claims. By way of non-limiting example, the illustrated embodiments are directed toward illuminating a moving web by dithering a beam in one-dimension. It will be appreciated that the beam can be dithered in two dimensions, for example, in order to illuminate non-moving object and/or to illuminate an object that is imaged by a planar field of view camera.

In view of the foregoing, what we claim is:

1. A system for illuminating an object to facilitate imaging thereof by an image acquisition device, the system comprising:
   A. a first radiation source that generates and transmits to a region of the object to be imaged a non-diffuse beam of imaging radiation having a non-point cross-section;
   B. a dithering element that moves the beam such that each point in the region of the object to be imaged is illuminated at substantially the same angle by multiple rays from the beam during an image frame acquisition period of the image acquisition device.

2. A system for illuminating an object to facilitate imaging thereof by an image acquisition device, the system comprising:
   A. a first radiation source that generates and transmits to a region of the object to be imaged a non-diffuse beam of imaging radiation having a non-point cross-section;
   B. a dithering element that moves the beam such that the region of the object to be imaged is illuminated at substantially the same angle by multiple rays from the beam during an image frame acquisition period of the image acquisition device,
   C. wherein the beam is incident on the object at a grazing angle with respect to the portion of the object to be imaged.

3. A system for illuminating an object to facilitate imaging thereof by an image acquisition device the system comprising:
   A. a first radiation source that generates and transmits to a region of the object to be imaged a non-diffuse beam of imaging radiation having a non-point cross-section,
   B. a dithering element that moves the beam such that the region of the object to be imaged is illuminated at substantially the same angle by multiple rays from the beam during an image frame acquisition period of the image acquisition device,
   C. wherein the beam provides dark field illumination of the region of the object to be imaged with respect to the image acquisition device.

4. A system for illuminating an object to facilitate imaging thereof by an image acquisition device, the system comprising:
   A. a first radiation source that generates and transmits to a region of the object to be imaged a non-diffuse beam of imaging radiation having a non-point cross-section;
   B. a dithering element that moves the beam such that the region of the object to be imaged is illuminated at substantially the same angle by multiple rays from the beam during an image frame acquisition period of the image acquisition device,
   C. wherein the first radiation source generates and transmits to the region of the object to be imaged a plurality of non-diffuse beams of imaging radiation, each having a non-point cross-section, and each illuminating the region at a different angle than the others.

5. A system according to claim 1, wherein the first radiation source generates and transmits to the region of the object to be imaged a beam of imaging radiation having a substantially linear cross-section.

6. A system according to claim 1, wherein the dithering element comprises any of a lens and a mirror.

7. A system according to claim 1, wherein the dithering element moves the beam in an oscillatory manner across the region of the object to be imaged.

8. A system according to claim 1, wherein the first radiation source comprises a source of coherent imaging radiation.

9. A system according to claim 8, wherein the first radiation source comprises a laser.

10. A system for illuminating an object to facilitate imaging thereof by an image acquisition device, the system comprising:
    A. a first radiation source that generates and transmits to a region of the object to be imaged a coherent beam of light having a non-point cross-section, the beam providing dark field illumination with respect to the image acquisition device;
    B. the first radiation source including a dithering element that moves the beam such that the region of the object to be imaged is illuminated at substantially the same angle by multiple rays from the beam during an image frame acquisition period of the image acquisition device, the beam moving in an oscillatory manner across the portion of the object to be imaged.

11. A system for illuminating an object to facilitate imaging thereof by an image acquisition device, the system comprising:
    A. a first radiation source that generates and transmits to a region of the object to be imaged a non-diffuse beam of imaging radiation having a non-point cross-section;
    B. the first radiation source including a dithering element that moves the beam such that the region of the object to be imaged is illuminated at substantially the same angle by multiple rays of the beam during an image frame acquisition period of the image acquisition device; and
    C. a second radiation source for illuminating at least the region of the object to be imaged with diffuse light.

12. A system according to claim 11, wherein the second radiation source illuminates the region of the object to be imaged at a grazing angle.

13. A system according to claim 11, wherein the second radiation source provides—with respect to the image acquisition device—dark field illumination of the region of the object to be imaged.

14. A system according to claim 11, wherein the second radiation source illuminates the region of the object to be imaged at an angle different from that at which the first radiation source transmits the beam to the object.

15. A method for illuminating an object to facilitate imaging thereof by an image acquisition device, the method comprising the steps of:
    A. illuminating a region of the object to be imaged with a non-diffuse beam of imaging radiation having a non-point cross-section; and
    B. moving that beam such that each point the region of the object to be imaged is illuminated at substantially the same angle by multiple rays during an image frame acquisition period of the image acquisition device.

16. A method for illuminating an object to facilitate imaging thereof by an image acquisition device, the method comprising the steps of:
    A. illuminating a region of the object to be imaged with a non-diffuse beam of imaging radiation having a non-point cross-section: and B. moving that beam such that the region of the object to be imaged is illuminated at substantially the same angle by multiple rays during an image frame acquisition period of the image acquisition device, C. wherein the illuminating step comprises illuminating the object by transmitting the beam at a grazing angle with respect to the region of the object to be imaged.

17. A method for illuminating an object to facilitate imaging thereof by an image acquisition device, the method comprising the steps of:

A. illuminating a region of the object to be imaged with a non-diffuse beam of imaging radiation having a non-point cross-section; and B. moving that beam such that the region of the object to be imaged is illuminated at substantially the same angle by multiple rays during an image frame acquisition period of the image acquisition device, C. wherein the illuminating step comprises illuminating the object by transmitting the beam to the object so as to provide—with respect to the image acquisition device—dark field illumination of the region of the object to be imaged.

18. A method for illuminating an object to facilitate imaging thereof by an image acquisition device, the method comprising the steps of:

A. illuminating a region of the object to be imaged with a non-diffuse beam of imaging radiation having a non-point cross-section; and B. moving that beam such that the region of the object to be imaged is illuminated at substantially the same angle by multiple rays during an image frame acquisition period of the image acquisition device, C. wherein the illuminating step comprises illuminating the object with a plurality of non-diffuse beams of imaging radiation, each having a non-point cross-section, where each beam illuminates the object at a different angle than the other beams.

19. A method according to claim 15, comprising the step of illuminating the object with a beam of non-diffuse radiation having a substantially linear cross-section.

20. A method according to claim 15, comprising the step of moving the beam with any of lens and a mirror.

21. A method according to claim 15, comprising the step of moving the beam in an oscillatory manner across the region of the object to be imaged.

22. A method according to claim 15, comprising the step of illuminating the object with coherent imaging radiation.

23. A method according to claim 22, comprising the step of illuminating the object with a laser.

24. A method for illuminating an object to facilitate imaging thereof by an image acquisition device, the method comprising the steps of A. illuminating a region of the object to be imaged with a coherent beam of light having a non-point cross-section, the beam providing dark field illumination with respect to the image acquisition device; and B. moving the beam in an oscillatory manner such that the region of the object to be imaged is illuminated at substantially the same angle by multiple rays during an image frame acquisition period of the image acquisition device.

25. A method for illuminating an object to facilitate imaging thereof by an image acquisition device, the method comprising the steps of A. illuminating a region of the object to be imaged with a non-diffuse beam of imaging radiation having a non-point cross-section;

B. moving the beam such that the region of the object to be imaged is illuminated at substantially the same angle by multiple rays during an image frame acquisition period of the image acquisition device; and C. illuminating at least the region of the object to be imaged with diffuse light.

26. A method according to claim 25, comprising the step of illuminating the object at a grazing angle with the diffuse light.

27. A method according to claim 25, comprising the step of illuminating the object with diffuse radiation for dark field imaging.

28. A method according to claim 25, comprising the step of illuminating the object a differing angles with each of the diffuse and non-diffuse radiation.

29. A system for illuminating an object to facilitate imaging thereof by an image acquisition device, the system comprising:

A. a first radiation source that generates and transmits to a region of the object to be imaged a non-diffuse beam of imaging radiation having a non-point cross-section;

B. the first radiation source including a dithering element that moves the beam such that the region of the object to be imaged is illuminated at substantially the same angle by multiple rays of the beam during an image frame acquisition period of the image acquisition device; and C. the first radiation source focussing the non-diffuse beam so that it has a wider cross-section in regions from which radiation reflected from the object is forward-scattered to the image acquisition device and has a narrower cross-section in regions from which radiation reflected from the object is back-scattered to the image acquisition device.

30. A system according to claim 29, wherein the first radiation source focusses the non-diffuse beam so that it is substantially 3 to 5 times wider at a point from which radiation reflected from the object is forward-scattered to the image acquisition device than at a point from which radiation reflected from the object is back-scattered to the image acquisition device.

* * * * *